United States Patent
Kovanyine Lax et al.

(10) Patent No.: US 7,981,884 B2
(45) Date of Patent: Jul. 19, 2011

(54) PROCESS FOR THE PREPARATION OF OLANZAPINE

(75) Inventors: Györgyi Kovanyine Lax, Budapest (HU); Gábor Nemeth, Budapest (HU); György Krasznay, Budapest (HU); Norbert Mesterhazy, Szombathely (HU); Kálmán Nagy, Budapest (HU); Györgyi Vereczkeyné Donáth, Budapest (HU); Zsuzsanna Szent-Kirallyi, Budapest (HU)

(73) Assignee: Egis Gyogyszergyar Nyilvanosan Mukodo Reszvenytarsasag, Budapest (HU)

( * ) Notice: Subject to any disclaimer, the term of this patent is extended or adjusted under 35 U.S.C. 154(b) by 310 days.

(21) Appl. No.: 12/093,344

(22) PCT Filed: Nov. 10, 2006

(86) PCT No.: PCT/HU2006/000096
§ 371 (c)(1),
(2), (4) Date: Oct. 2, 2008

(87) PCT Pub. No.: WO2007/054750
PCT Pub. Date: May 18, 2007

(65) Prior Publication Data
US 2009/0137563 A1    May 28, 2009

(30) Foreign Application Priority Data
Nov. 11, 2005    (HU) ..................... 0501046

(51) Int. Cl.
*A61P 25/18*    (2006.01)
*A61K 31/5513*    (2006.01)
*C07D 495/04*    (2006.01)

(52) U.S. Cl. ..................... 514/220; 540/557

(58) Field of Classification Search .............. 514/220; 540/557
See application file for complete search history.

(56) References Cited

U.S. PATENT DOCUMENTS

| | | | |
|---|---|---|---|
| 5,703,232 A | 12/1997 | Bunnell et al. | 540/557 |
| 2004/0048854 A1 | 3/2004 | Patel et al. | 514/220 |
| 2005/0159408 A1 | 7/2005 | Dolitzky et al. | 514/220 |

*Primary Examiner* — Brenda Coleman
(74) *Attorney, Agent, or Firm* — Jonathan Myers; Andrew Wilford

(57) ABSTRACT

The invention relates to a process for the preparation of 2-methyl-4-(4-methylpiperazin-1-yl)-10H-thieno-[2,3-b][1,5]benzodiazepine (olanzapine) of the formula (I) by reacting 4-amino-2-methyl-10H-thieno[2,3-b][1/5]benzodiazepine hydrochloride of the formula (II) with N-methylpiperazine in an organic solvent, which comprises carrying out the reaction in the mixture of toluene and 1,3-dimethyl-2-imidazolidinone. The invention also encompasses new 2-methyl-4-(4-methylpiperazin-1-yl)-10H-thieno[2,3-b] [1,5]benzodiazepine dihydrochloride trihydrate of the formula (IB), the preparation thereof and pharmaceutical compositions comprising said new compound.

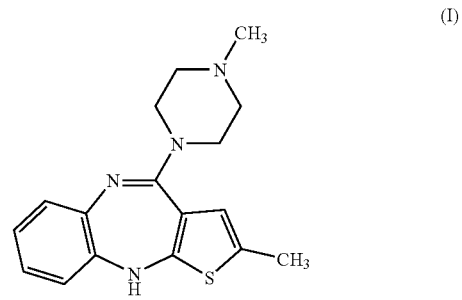

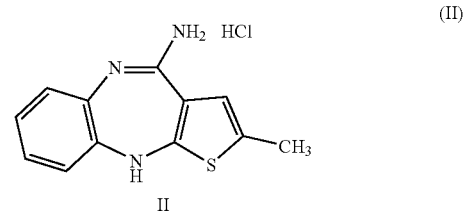

17 Claims, 2 Drawing Sheets

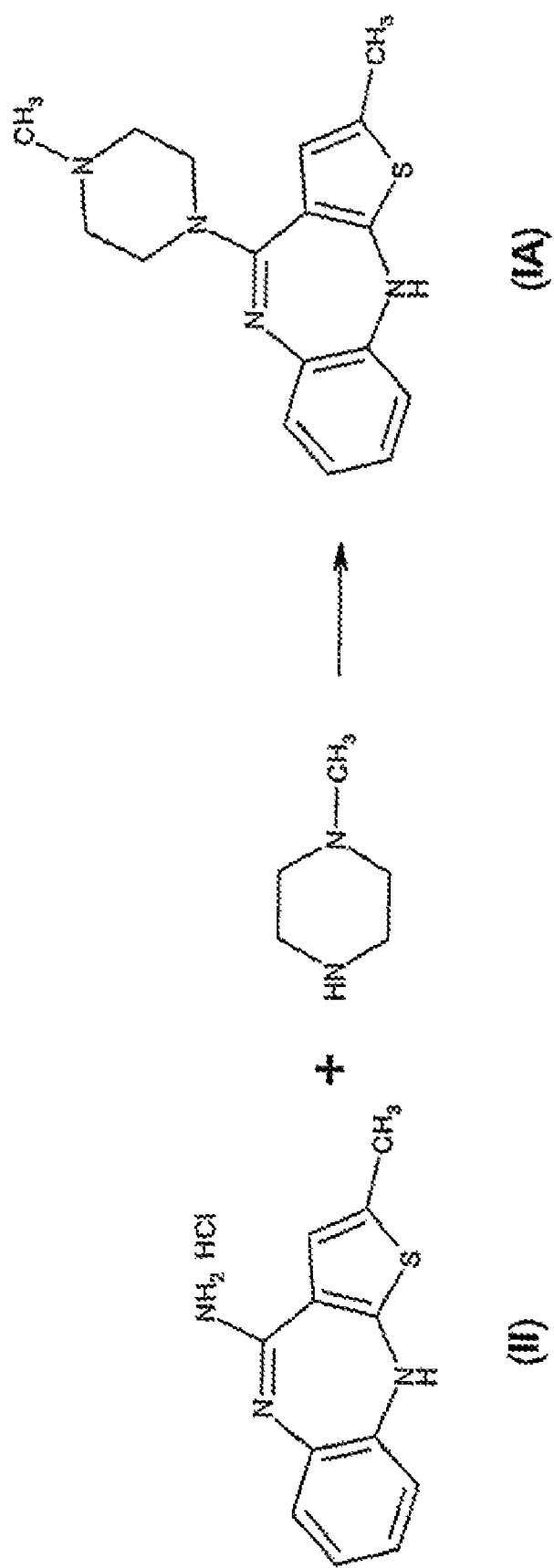

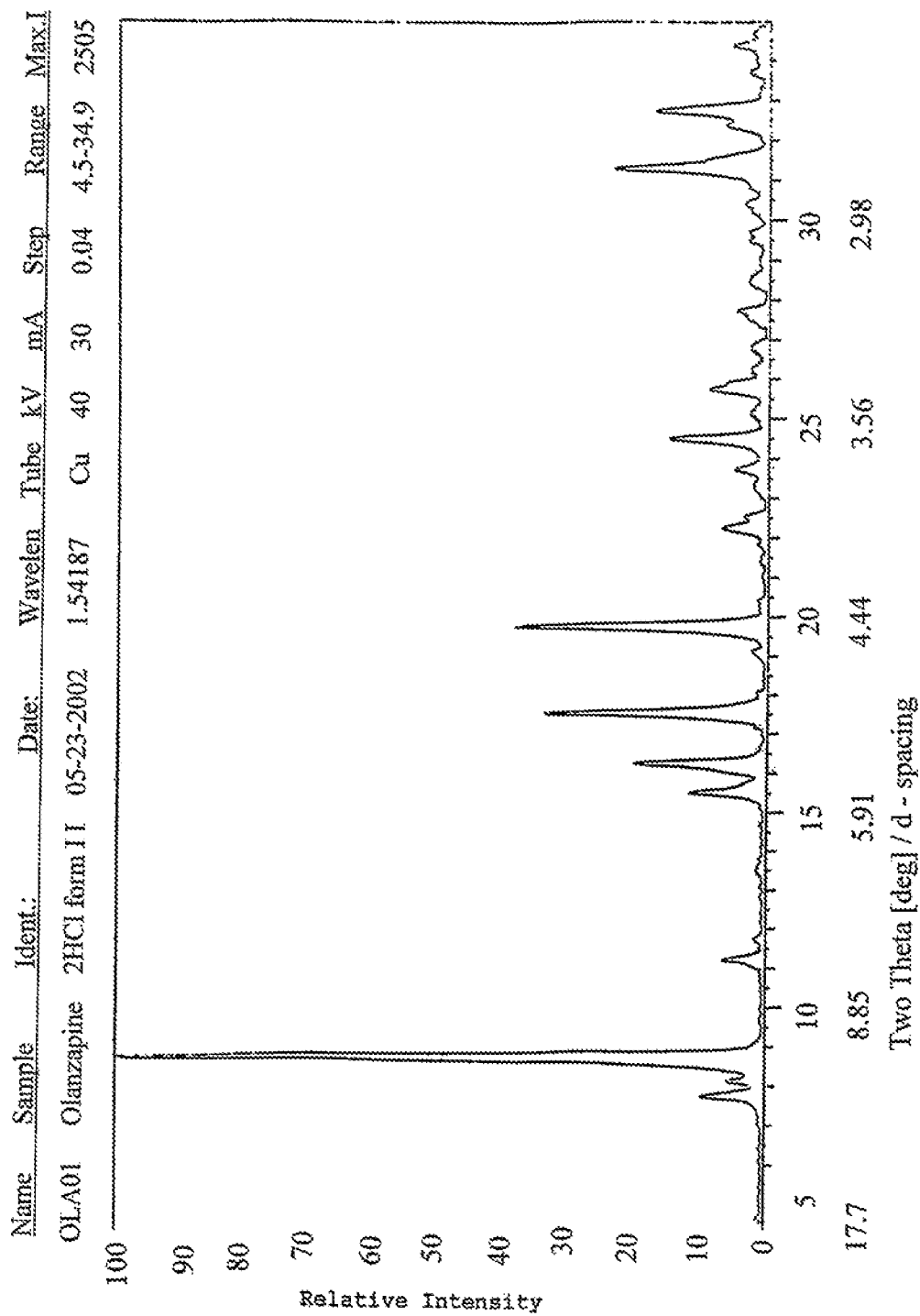

PROCESS FOR THE PREPARATION OF OLANZAPINE

CROSS REFERENCE TO RELATED APPLICATIONS

This application is the US national phase of PCT application 2006/000096, filed 10 Nov. 2006, published 18 May 2007 as WO 2007/054750, and claiming the priority of Hungarian patent application PO501046 itself filed 11 Nov. 2005, whose entire disclosures are herewith incorporated by reference.

TECHNICAL FIELD OF THE INVENTION

The present invention relates to an improved process for the preparation of olanzapine, to a new olanzapine salt hydrate and the preparation thereof. The invention also relates to pharmaceutical compositions containing said new olanzapine salt hydrate and the use thereof for the treatment of psychotic conditions.

BACKGROUND OF THE INVENTION

It is known that 2-methyl-4-(4-methylpiperazin-1-yl)-10H-thieno[2,3-b][1,5]benzodiazepine of the formula (IA)

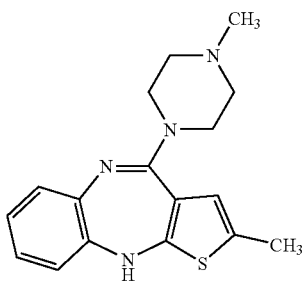

(hereinafter referred to as "olanzapine") is a valuable antipsychotic drug.

Olanzapine was described for the first time in EP 454,436. According to the final step of the synthesis provided in said patent specification 4-amino-2-methyl-10H~thieno[2,3-b]-[1,5]benzodiazepine hydrochloride of the formula (II)

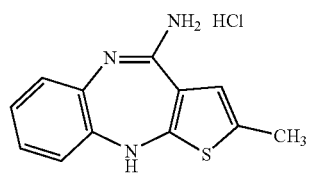

is reacted with an excess amount of N-methylpiperazine for 20 hours under nitrogen atmosphere, in a 1:1 mixture of toluene and dimethyl sulfoxide, at the boiling point of the mixture, and the reaction mixture is cooled to 50° C. Olanzapine is crystallized by adding some water to the mixture and the thus-obtained crude product is recrystallized from acetonitrile. The desired olanzapine is obtained in a yield of 48%. The reaction is depicted in reaction scheme 1 as set forth in FIG. 1.

International patent application WO 2004/094433 A1 provides two new polymorphic forms of olanzapine dihydrochloride, and furthermore provides a new polymorphic olanzapine monohydrochloride.

European patent specification No. 733,635 discloses the preparation of olanzapine of so-called "technical quality". This process is also carried out according to reaction scheme 1, with the difference that six times the amount of dimethyl sulfoxide is used at a temperature of 120° C. The reaction is detected by HPLC. The reaction is performed until 5% of residual starting substance of the formula (II) has remained in the mixture. Then it is cooled to 20° C. and olanzapine is crystallized at 5° C. by subsequently adding a tenfold amount of methanol and a threefold amount of water to the mixture. The yield of the thus-obtained crude olanzapine base amounts to 76.7%.

The inventors of the present invention have repeated the above reaction carried out in dimethyl sulfoxide or in a 1:1 mixture of toluene and dimethyl sulfoxide as specified in the prior art. During the reproduction it has been found that an undesirable amount of olanzapine N-oxide of the formula (III)

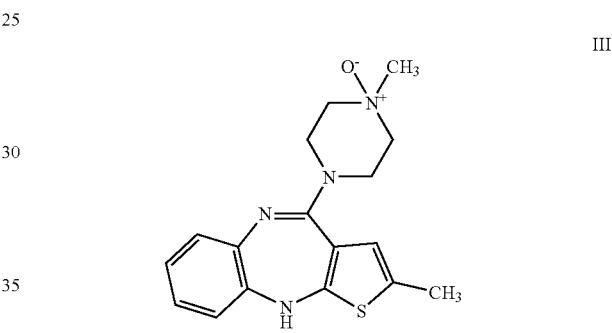

is formed even if the reaction is carried out under inert gas atmosphere (e.g. nitrogen or argon). This is even more surprising because—according to the experiments of the inventors of the present invention—dimethyl sulfoxide does not oxidize olanzapine, in spite of that according to many publications available in the literature dimethyl sulfoxide acts as an oxidizing agent. In spite of this fact, if dimethyl sulfoxide is applied as solvent for the reaction depicted in reaction scheme 1, a higher amount of the undesired the N-oxide of the formula (III) is formed. The stricter and stricter analytical requirements established for pharmaceutical substances call for the strongest possible decrease in the amount of impurities, such as the N-oxide of the formula (III). According to the experiences of the inventors of the present invention the amount of the impurity of the formula (III) being present in the pharmaceutical composition containing olanzapine as active ingredient increases during storage. Due to the structural similarity between olanzapine and its N-oxide of the formula (III) the separation of the two compounds—that is the removal of the impurity of the formula (III)—is cumbersome on the one part and inevitably leads to losses on the other.

OBJECT OF THE INVENTION

It is the object of the present invention to elaborate an industrially applicable process for the preparation of olanzapine, which enables the minimalization of the formation of N-oxide of the formula (III).

SUMMARY OF THE INVENTION

The above object is solved by the present invention.

The present invention is based on the recognition that if instead of dimethyl sulfoxide the reaction is carried out in the mixture of another dipolar aprotic solvent—that is in 1,3-dimethyl-2-imidazolidinone and toluene, olanzapine N-oxide of the formula (III) is formed in a considerably smaller amount, which is not problematical in respect to the stability of the composition, because even during long-term storage it does not increase beyond the limit permitted in pharmaceutical compositions.

DETAILS OF THE INVENTION

According to an aspect of the present invention there is provided a process for the preparation of 2-methyl-4-(4-methylpiperazin-1-yl)-10H-thieno-[2,3-b][1,5]benzodiazepine (olanzapine) of the formula (IA) by reacting 4-amino-2-methyl-1-10H-thieno[2,3-b][1,5]benzodiazepine hydrochloride of the formula (II) with N-methylpiperazine in an organic solvent, which comprises carrying out the reaction in the mixture of toluene and 1,3-dimethyl-2-imidazolidinone.

1,3-Dimethyl-2-imidazolidinone possesses favorable pharmaceutical properties. It is a strongly polar aprotic solvent, which is stable in the presence of acids and alkalis even at high temperatures, and it is not corrosive. The boiling and ignition points of 1,3-dimethyl-2-imidazolidinone are high (225° C. and 120° C., respectively), $LD_{50}$=2840 mg/kg. Due to its high permittivity and solvation effects 1,3-dimethyl-2-imidazolidinone activates the reagents. A further advantage of the application of 1,3-dimethyl-2-imidazolidinone resides in the fact that it eliminates the oxidative, unpleasant environmental and labor safety properties of dimethyl sulfoxide.

During the reaction N-methyl piperazine is preferably applied in an excess quantity.

The reaction is preferably carried out in a 3:1 mixture, particularly preferably in a 1:1 mixture, more preferably in a 2:1 mixture of toluene and 1,3-dimethyl-2-imidazolidinone. The reaction is carried out at a temperature between 100° C. and 130° C. The reaction is performed under an inert gas atmosphere (preferably nitrogen or argon).

A further advantage of the process according to the invention resides in the fact that the reaction can be performed in a considerably shorter period of time (within 8 to 11 hours, preferably within 9 hours) than the one provided in the prior art, which is carried out in dimethyl sulfoxide medium and takes 20 hours. The olanzapine base obtained after evaporating the reaction mixture is of high purity. If desired, the product can be recrystallized from acetonitrile.

According to another aspect of the present invention there is provided a process for the preparation of 2-methyl-4-(4-methylpiperazin-1-yl)-10H-thieno-[2,3-b][1,5]benzodiazepine dihydrochloride trihydrate of the formula (IB),

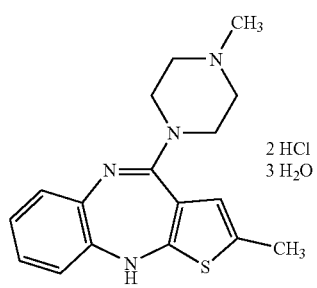

which comprises reacting 2-methyl-4-(4-methylpiperazin-1-yl-10H-thieno-[2,3-b][1,5]benzodiazepine of the formula (IA) in an aqueous ethanol medium with hydrogen chloride.

The reaction can preferably be carried out in an 8:2 mixture, particularly preferably in a 9:1 mixture of ethanol and water.

One can also proceed by adding an aqueous hydrogen chloride solution to the suspension of 2-methyl-4-(4-methylpiperazin-1-yl)-10H-thieno[2,3-b][1,5]benzodiazepine of the formula (IA) in ethanol. Preferably 37% aqueous hydrogen chloride solution is applied.

The above process enables the preparation of 2-methyl-4-(4-methylpiperazin-1-yl)-10H-thieno[2,3-b][1,5]benzodiazepine dihydrochloride trihydrate of the formula (IB) in a purity as high as 99.9% by HPLC in a yield as excellent as 83.5%.

According to a further aspect of the present invention there is provided the new 2-methyl-4-(4-methylpiperazin-1-yl)-10H-thieno[2,3-b][1,5]benzodiazepine dihydrochloride trihydrate of the formula (IB).

BRIEF DESCRIPTION OF THE DRAWINGS

FIG. 1 is a reaction scheme showing the reaction of 4-amino-2-methyl-10H-thieno[2,3-b]-[1,5]benzodiazepine hydrochloride of the formula (II) with N-methyl-piperazine to yield 2-methyl-4-(4-methylpiperazin-1-yl)-10H-thieno[2,3-b][1,5]benzodiazepine of the formula (IA).

FIG. 2 is an X-Ray diffraction pattern of 2-methyl-4-(4-methylpiperazin-1-yl)-10H-thieno[2,3-b][1,5]-benzodiazepine dihydrochloride trihydrate of the formula)(IB).

The X-ray powder diffraction pattern of 2-methyl-4-(4-methylpiperazin-1-yl)-10H-thieno[2,3-b][1,5]-benzodiazepine dihydrochloride trihydrate of the formula (IB) measured by using $CuK_{\alpha}$ radiation corresponds to the X Ray powder diffraction pattern in FIG. 2 and can be characterized by the X-ray powder diffraction pattern expressed below:

Position of diffraction lines and relative intensities (>5%)

| Peak No. | 2*th [deg] | D(hkl) [L] | I(abs) [cps] | I(rel) [%] |
| --- | --- | --- | --- | --- |
| 1 | 7.78 | 11.3638 | 219 | 8.74 |
| 2 | 8.17 | 10.8222 | 124 | 4.95 |
| 3 | 8.79 | 10.0557 | 2505 | 100.00 |
| 4 | 11.26 | 7.8611 | 143 | 5.71 |
| 5 | 15.54 | 5.7012 | 265 | 10.58 |
| 6 | 16.28 | 5.4444 | 478 | 19.08 |
| 7 | 17.55 | 5.0524 | 817 | 32.61 |
| 8 | 19.78 | 4.4885 | 933 | 37.25 |
| 9 | 22.26 | 3.9945 | 153 | 6.11 |
| 10 | 24.51 | 3.6315 | 348 | 13.89 |
| 11 | 25.75 | 3.4605 | 202 | 8.06 |
| 12 | 25.93 | 3.4362 | 131 | 5.23 |
| 13 | 31.30 | 2.8580 | 558 | 22.28 |
| 14 | 31.53 | 2.8375 | 202 | 8.06 |
| 15 | 32.38 | 2.7651 | 145 | 5.79 |
| 16 | 32.74 | 2.7355 | 404 | 16.13 |

The above data were determined under the following conditions:
Equipment:
PHILIPS—XPERT PW 3710 powder diffractometer
Radiation: Cu Kα (λ: 1.54190 L)
Monochromator: graphite
Excitation voltage: 40 kV
Anode current: 30 mA
Method:
Standard reference substance: SRM 675
Mica Powder (synthetic fluorophlogopite), serial number: 981307.
The measurement was continuous: Θ/2Θ scan:
4.5°-35.00° 2Θ
Step size: 0.02-0.04°
Sample: surface plain, width 0.5 mm, in quartz kvarz sample holder, measured and stored at room temperature.

2-Methyl-4-(4-methylpiperazin-1-yl)-10H-thieno[2,3-b][1,5]-benzodiazepine dihydrochloride trihydrate (olanzapine dihydrochloride trihydrate) of the formula (IB) is a highly advantageous crystalline form. The product is a morphologically uniform, stable substance having excellent filtration, drying and storing characteristics, and its storage does not require special circumstances.

According to a further aspect of the present invention there is provided a pharmaceutical composition comprising as active ingredient 2-methyl-4-(4-methylpiperazin-1-yl)-10H-thieno[2,3-b][1,5]benzodiazepine dihydrochloride trihydrate of the formula (IB) in admixture with inert solid or liquid pharmaceutical carriers and/or auxiliary agents.

According to a still further aspect of the present invention there is provided a process for the preparation of a pharmaceutical composition, which comprises admixing 2-methyl-4-(4-methylpiperazin-1-yl)-10H-thieno-[2,3-b][1,5]benzodiazepine dihydrochloride trihydrate of the formula (IB) with a pharmaceutically acceptable solid or liquid carrier and/or auxiliary agent and bringing the mixture to galenic form.

The pharmaceutical compositions according to the invention can be prepared by methods conventionally applied in the pharmaceutical industry. The pharmaceutical compositions according to the invention can be administered orally (e.g. tablets, coated tablets, capsules, pilules, solutions, suspensions or emulsions), rectally (e.g. suppositories), parenterally (e.g. intravenously, intraperitoneally, etc.) or transdermally.

The pharmaceutical compositions according to the invention may contain usual pharmaceutical carriers and/or auxiliary agents. As carrier magnesium carbonate, magnesium stearate, talc, sucrose, lactose, pectin, dextrin, starch, gelatine, tragacanth, methyl cellulose, sodium carboxymethyl cellulose, low melting wax, cocoa butter etc. can be used. In case of capsules the carrier is generally the wall of the capsule so that no additional carrier is needed. As oral administration form the lozenge and sachet can also be mentioned. Tablets, powders, capsules, pilules, sachets and lozenges are solid forms particularly suitable for oral administration.

Suppositories may contain low melting waxes (e.g. mixtures of fatty acid triglycerides or cocoa butter) as carrier. Suppositories can be prepared by melting the wax, homogeneously distributing the active ingredient in the melt, pouring the melt homogenous mixture into mould forms of suitable size and form, and allowing the mixture to solidify under cooling.

Tablets can be prepared by admixing the active ingredient with suitable carriers in the appropriate ratio and pressing the mixture into tablets of suitable size and form.

Powders are prepared by admixing the finely powdered active ingredient with finely powdered carriers.

As liquid pharmaceutical compositions optionally sustained release solutions, suspensions and emulsions can be mentioned. Aqueous solutions and aqueous propylene glycol solutions are advantageous. Liquid pharmaceutical compositions suitable for parenteral administration can be preferably prepared in the form of aqueous polyethylene glycol solutions.

Aqueous solutions suitable for oral administration can be produced by dissolving the active ingredient in water and adding suitable coloring, aromatizing, stabilizing agents and thickeners.

Aqueous suspensions suitable for oral administration can be prepared by suspending the active ingredient in water in presence of a viscous substance (e.g. natural or artificial gums, resins, methyl cellulose, sodium carboxymethyl cellulose or other known suspending agents).

Another type of solid pharmaceutical compositions can be converted into liquid compositions immediately before use and administered orally into the organism in liquid form. Solutions, suspensions or emulsions can be mentioned as such liquid forms of administration which contain, in addition to the active ingredient, coloring agents, aromatizing agents, preservatives, buffers, artificial or natural sweeteners, dispersing agents, thickeners, etc.

The pharmaceutical compositions of the present invention are preferably prepared in dosage unit form. Such dosage units contain the desired amount of the active ingredient. The dosage units can be put on the market in packages containing discrete amounts of the compositions (e.g. packed tablets, capsules or powders in vials or ampoules). The term "dosage unit" relates to the capsules, tablets, lozenges, sachets per se and also to the packaging which contains the suitable number of dosage units.

The active ingredient may be released from the is pharmaceutical compositions according to the present invention immediately or in a delayed manner.

The pharmaceutical compositions according to the present invention usually contain about 0.1-100 mg, preferably about 0.5-50 mg of active ingredient.

According to a still further aspect of the present invention there is provided the use of 2-methyl-4-(4-methylpiperazin-1-yl)-10H-thieno[2,3-b]-[1,5]benzodiazepine dihydrochloride trihydrate of the formula (IB) as a pharmaceutically active ingredient.

According to a particular aspect of the present invention there is provided the use of 2-methyl-4-(4-methylpiperazin-1-yl)-10H-thieno[2,3-b]-[1,5]benzodiazepine dihydrochloride trihydrate of the formula (IB) for the preparation of pharmaceutical compositions having antipsychotic activity.

According to a still further aspect of the present invention there is provided a method for the treatment of psychotic conditions, which comprises administering to a patient in need of such treatment a pharmaceutically active amount of 2-methyl-4-(4-methylpiperazin-1-yl)-10H-thieno[2,3-b][1,5]benzodiazepine dihydrochloride trihydrate of the formula (IB).

The invention involves the following advantages:
During the preparation of olanzapine base a lower amount of the undesired N-oxide contamination of the formula (III) is formed;
The process provides the preparation of high-purity olanzapine in an excellent yield;
During the preparation of olanzapine a solvent having good physical properties and suitable in respect of environmental and labor safety considerations is applied;
olanzapine can be prepared in a considerably shorter period of time;

the new olanzapine dihydrochloride trihydrate according to the invention is a morphologically uniform crystalline form having excellent filtration, drying and storing characteristics, which can be used to advantage in the pharmaceutical industry.

Further details of the present invention are provided in the following examples without limiting the scope of protection to said examples.

Example 1

Olanzapine Base; (IA)

To a mixture of 53.77 g (0.2 mole) of 4-amino-2-methyl-10H-thieno[2,3-b][1,5]benzodiazepine hydrochloride, 538 cm$^3$ of toluene and 269 cm$^3$ of DMI (1,3-dimethyl-2-imidazolidinone) 186 cm$^3$ (167.4 g, 1.67 mole) of N-methylpiperazine are added under stirring, an argon stream is generated, and the reaction mixture is heated to the boiling point (126° C.) with the aid of an oil bath.

The mixture is allowed to boil for 9 hours until 1% amount of starting substance can be detected by HPLC. It is then evaporated at a temperature of 50-55° C. under 5-10 mbar. The is thus-obtained residue is cooled with ice-water to a temperature of about 3-5° C., 320 cm$^3$ of water are dropwise added to it, while the product continuously separates from the reaction mixture. It is stirred further at a temperature of 5° C. for 1 hour, filtered, washed with 120 cm$^3$ of water and dried with the aid of an infrared lamp. Thus 56 g (89.6%) of base are obtained. (M.p.: 189-193° C., HPLC: 98%), which is recrystallized from a 14-times amount of acetonitrile to yield 42.6 g (76%) of the desired compound. M.p.: 194-196° C., HPLC: 99.87%.

$^1$HNMR (DMSO, i500): ?: 7.59 (s, IH), 6.84 (m, IH), 6.81 (m, IH), 6.79 (dd, IH),), 6.69 (dd, IH), 6.33 (d, IH, J=1.1 Hz), 3.33 (m, 4H), 2.37 (t, 4H), 2.27 (d, 3H, J=1.1 Hz), 2.20 (s, 3H).

Example 2

Olanzapine Base: (IA)

To a mixture of 5 g (0.019 mole) of 4-amino-2-methyl-10H-thieno[2,3-b][1,5]benzodiazepine hydrochloride, 50 cm$^3$ of toluene and 50 cm$^3$ of DMI 17.5 cm$^3$ of N-methylpiperazine are added under stirring, an argon stream is generated, and the reaction mixture is kept boiling for 11 hours at a temperature of 130° C. with the aid of an oil bath. Then it is evaporated at a temperature between 50° C. and 55° C. under 5-10 mbar.

The thus-obtained brown residue is cooled to a temperature of about 3-5° C. with the aid of ice water, under stirring. Then 30 cm$^3$ of water are dropped to it at the same temperature. It is stirred further for 1 hour, washed with water and dried. Thus 4.5 g (77.1%) of the desired compound are obtained. M.p.: 193-196° C., HPLC: 98.8%.

Example 3

Olanzapine Base: (IA)

To a mixture of 26.58 g (0.1 mole) of 4-amino-2-methyl-10H-[1,5]-benzodiazepine hydrochloride, 266 cm$^3$ of toluene and 83 cm$^3$ of DMI, 93 cm$^3$ of N-methylpiperazine are added under stirring, an argon stream is generated, and the mixture is boiled in an oil bath at a temperature of 120° C. for 9 hours. The reaction mixture is then evaporated at a temperature of 50-55° C. under 5-10 mbar.

The thus-obtained brown residue is cooled to a temperature of about 3-5° C. with ice water, under stirring, and 160 cm$^3$ of water are dropped to it at the same temperature. The mixture is stirred further for 1 hour at a temperature of about 5° C., filtered, washed with 60 cm$^3$ of water and dried. Thus 23.7 g (76%) of the desired compound are obtained. M.p.: 194-196° C., HPLC: 99.18%.

Example 4

Olanzapine Dihydrochloride Trihydrate; (IB)

42.6 g (0.14 mole) of olanzapine base are suspended in a mixture of 680 cm$^3$ of ethanol and 68 cm$^3$ of water, and 29.2 cm$^3$ of 37% hydrogen chloride are dropped to the suspension under stirring. During the addition of hydrogen chloride the suspension turns into solution, then the yellow crystalline product separates continuously. The mixture is stirred further for 2 hours. The suspension is then filtered, washed with twice with 15 cm3 each of cooled ethanol and dried under an infrared lamp. Thus 51.4 g (83.5%) of the desired product are obtained. M.p. (Koffler): 201-240° C. (continuous decomposition).

HPLC: 99.9%.

Example 5

Olanzapine Dihydrochloride Trihydrate; (IB)

To a suspension of 5 g (0.016 mole) of olanzapine base in 80 ml of ethanol 3.3 ml of 37% hydrogen chloride solution are dropped at a temperature of 25° C., under vigorous stirring (1.46 g, 0.04 mole) under 2 hours. The mixture is then stirred further for 2 hours at a temperature of 25° C., to the thus-obtained suspension 16 ml of water are dropped, and the suspension is stirred at a temperature of 25° C. for 24 hours. The thus-obtained yellow crystalline substance is filtered off and dried. Thus 5.8 g (82%) of the desired compound are obtained.

Example 6

Olanzapine Dihydrochloride Trihydrate: (IB)

To a suspension of 5 g (0.016 mole) of olanzapine base in 80 ml of ethanol 3.3 ml of 37% hydrogen chloride solution (1.46 g# 0.04 mole) are dropped within 2 hours at 25° C. under vigorous stirring. Then 16 ml of water are added to the mixture. During the addition of water a solution is formed, and in half an hour crystals begin to separate. The suspension is stirred for 24 hours, filtered and dried. Thus 4.2 g (60%) of the desired is compound are obtained.

Example 7

4-(2-Methyl-I0H-thieno[2,3-b][1,5]benzodiazepin-4-yl}-1-methylpiperazine-1-oxide (III) [olanzapine N-oxide]

5.0 g (0.016 mole) of olanzapine base are suspended in 50 cm3 of dichloromethane, the suspension is cooled to 0-5° C., and 4.05 g of 75% (3.03 g, 0.016 mole) of m-chloroperbenzoic acid are added to it. The mixture is stirred further first for 2 hours at a temperature of 0-5° C., then for 10 hours at 10-12°

C. and processed as follows: it is poured onto 100 cm³ of water under stirring and extracted 3 times with 150 cm³ each of dichloromethane. The organic phase is washed subsequently with sodium chloride solution and water. Following the extraction "N-oxide" separate from the aqueous phase in form of white precipitates. The mixture is then filtered. Thus 4.1 g (79.1%) of the desired substance are obtained. M.p.: 204-206° C., HPLC: 99.6%.

2.78 g of substance are obtained by the evaporation of the organic phase, which contains olanzapine base as well. Subjecting it to column chromatography in a 6:4 mixture of toluene and methanol a further amount of 1.6 g of substance is obtained, which is suspended in ether and recrystallized from ethanol. Thus a further amount of 0.8 g of product is obtained, HPLC: 99.7%.

Elementary analysis for the formula $C_{17}H_{20}N_4OS \times 1.5 H_2O=355.44$

|  | C % | H % | N % |
|---|---|---|---|
| Calculated: | 57.39 | 6.47 | 15.76 |
| Found: | 57.25 | 6.5 | 15.8 |

IR(KBr): 3213, 3051, 2945, 2915, 1588, 1563, 1466, 1416, 1283, 1220, 1136

$^1$HNMR (DMSO, i500): δ: 7.97 (s, IH), 6.85 (t, IH), 6.83 (t, IH), 6.81 (dd, IH),
6.73 (dd, IH), 6.39 (s, IH), 3.78 (d, 2H), 3.6 (t, 2H), 3.42 (t, 2H), 3.11 (s, 3H), 2.96 (d, 2H), 2.27 (S, 3H)

$^3$CNMR (DMSO, i500): δ: 157.04, 154.2, 144.27, 140.6, 128.33, 127.72, 123.86, 123.66, 122.66, 119.20, 117.78, 64.75, 60.37, 41.47, 15.27

According to mass spectrometry M+H is at 329, fragment ions can be found at the m/z values of 311, 285, 229.

The invention claimed is:

1. A process for the preparation of a compound of the formula (IA)

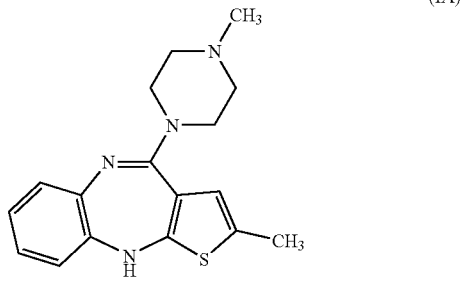

(IA)

which comprises the step of reacting a hydrochloride of the formula (II)

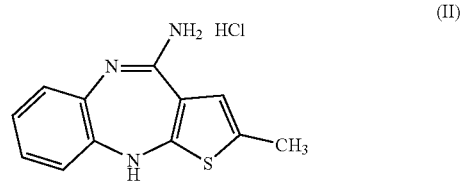

(II)

with N-methylpiperazine in an organic solvent, wherein the reaction is carried out in a mixture of toluene and 1,3-dimethyl-2-imidazolidinone.

2. A process as claimed in claim 1, which comprises using a 3:1 mixture by volume of toluene and 1,3-dimethyl-2-imidazolidinone.

3. A process as claimed in claim 1, which comprises using a 1:1 mixture by volume of toluene and 1,3-dimethyl-2-imidazolidinone.

4. A process as claimed in claim 1, which comprises using a 2:1 mixture by volume of toluene and 1,3-dimethyl-2-imidazolidinone.

5. A process as claimed in claim 1, which comprises carrying out the reaction at a temperature between 100° C. and 130° C.

6. A process as claimed in claim 1, which comprises carrying out the reaction within 8 to 11 hours.

7. A process as claimed in claim 6, which comprises carrying out the reaction within 9 hours.

8. A process for the preparation of a compound of the formula (IB),

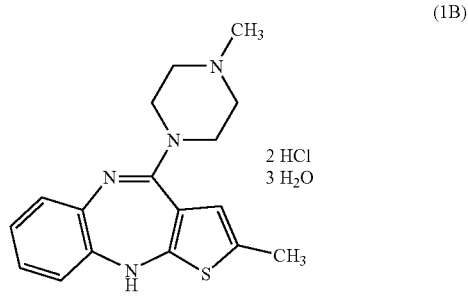

(IB)

which comprises the step of reacting a compound of the formula (IA)

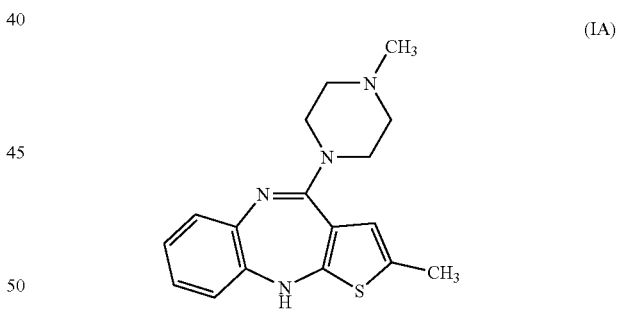

(IA)

with hydrogen chloride in an aqueous ethanol medium.

9. A process as claimed in claim 8, which comprises carrying out the reaction in a 8:2 mixture by volume of ethanol and water.

10. A process as claimed in claim 8, which comprises carrying out the reaction in a 9:1 mixture by volume of ethanol and water.

11. A process as claimed in claim 8, which comprises adding an aqueous hydrogen chloride solution to a suspension of the compound of the formula (IA) in ethanol.

12. A process as claimed in claim 11, which comprises using 37% aqueous hydrogen chloride solution.

13. A process as claimed in claim 8, which comprises carrying out the reaction at a temperature between 20° C. and 50° C.

14. A compound of the formula (IB)

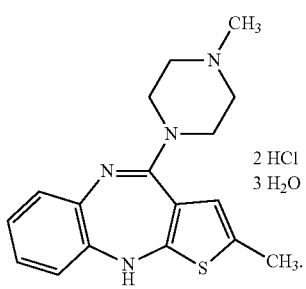

15. The compound of the formula (IB) as claimed in claim 14, characterized by the X-ray powder diffraction pattern measured using CuKα radiation corresponding to the X Ray diffraction pattern in FIG. 2 and expressed in the following Table:
Position of diffraction lines and relative intensities (>5%)

| Peak No. | 2*th [deg] | D(hkl) [L] | I(abs) [cps] | I(rel) [%] |
|---|---|---|---|---|
| 1 | 7.78 | 11.3638 | 219 | 8.74 |
| 2 | 8.17 | 10.8222 | 124 | 4.95 |
| 3 | 8.79 | 10.0557 | 2505 | 100.00 |
| 4 | 11.26 | 7.8611 | 143 | 5.71 |
| 5 | 15.54 | 5.7012 | 265 | 10.58 |
| 6 | 16.28 | 5.4444 | 478 | 19.08 |
| 7 | 17.55 | 5.0524 | 817 | 32.61 |
| 8 | 19.78 | 4.4885 | 933 | 37.25 |
| 9 | 22.26 | 3.9945 | 153 | 6.11 |
| 10 | 24.51 | 3.6315 | 348 | 13.89 |
| 11 | 25.75 | 3.4605 | 202 | 8.06 |
| 12 | 25.93 | 3.4362 | 131 | 5.23 |
| 13 | 31.30 | 2.8580 | 558 | 22.28 |
| 14 | 31.53 | 2.8375 | 202 | 8.06 |
| 15 | 32.38 | 2.7651 | 145 | 5.79 |
| 16 | 32.74 | 2.7355 | 404 | 16.13. |

16. Pharmaceutical compositions comprising as active ingredient a compound of the formula (IB) as defined in claim 14 in admixture with inert solid or liquid pharmaceutical carriers and/or auxiliary agents.

17. A method of treating a patient with a psychosis which comprises the step of administering to the patient in need of such treatment a therapeutically effective amount of the compound of the formula (IB) defined in claim 14.

* * * * *